(12) United States Patent
Siew Kuang Choong

(10) Patent No.: US 8,944,299 B2
(45) Date of Patent: Feb. 3, 2015

(54) MOBILE INTRAVENOUS ADMINISTRATION APPARATUS

(76) Inventor: Siow Kuang Ling Siew Kuang Choong, Johor (MY)

( * ) Notice: Subject to any disclaimer, the term of this patent is extended or adjusted under 35 U.S.C. 154(b) by 196 days.

(21) Appl. No.: 13/511,687

(22) PCT Filed: Nov. 24, 2010

(86) PCT No.: PCT/MY2010/000290
§ 371 (c)(1),
(2), (4) Date: Jun. 14, 2012

(87) PCT Pub. No.: WO2011/065812
PCT Pub. Date: Jun. 3, 2011

(65) Prior Publication Data
US 2012/0289927 A1    Nov. 15, 2012

(30) Foreign Application Priority Data
Nov. 24, 2009   (MY) ................................ PI20094994

(51) Int. Cl.
*A61M 5/14*   (2006.01)

(52) U.S. Cl.
CPC ........... *A61M 5/1411* (2013.01); *A61M 5/1415* (2013.01); *A61M 2005/1416* (2013.01)
USPC ..................... 224/148.2; 224/148.7; 224/576; 224/197

(58) Field of Classification Search
CPC ................. A61M 2005/1416; A61M 5/14244; A61M 2209/088
USPC ................... 224/576, 148.7, 148.2, 926, 197; 128/DIG. 6; D24/128
See application file for complete search history.

(56) References Cited

U.S. PATENT DOCUMENTS

| | | | | | |
|---|---|---|---|---|---|
| 2,723,665 | A | * | 11/1955 | Goldsmith | 128/877 |
| 3,547,322 | A | * | 12/1970 | Dawson et al. | 224/148.2 |
| 4,087,864 | A | * | 5/1978 | LaBove et al. | 2/102 |
| 4,438,763 | A | * | 3/1984 | Zablen | 128/845 |
| 5,097,255 | A | * | 3/1992 | Chen | 340/603 |
| 5,342,313 | A | * | 8/1994 | Campbell et al. | 604/153 |
| 5,626,270 | A | * | 5/1997 | Tseng | 224/148.7 |
| 5,676,294 | A | * | 10/1997 | Eklund et al. | 224/625 |
| 5,799,846 | A | * | 9/1998 | Pfleger | 224/148.7 |
| 2012/0132784 | A1 | * | 5/2012 | Dukes et al. | 248/690 |
| 2012/0228344 | A1 | * | 9/2012 | Neoh | 224/148.4 |
| 2013/0237915 | A1 | * | 9/2013 | Barrelli | 604/136 |

FOREIGN PATENT DOCUMENTS

FR    2832315 A1 *   5/2003

* cited by examiner

*Primary Examiner* — Justin Larson
(74) *Attorney, Agent, or Firm* — Foley & Lardner LLP

(57) ABSTRACT

The present invention relates to intravenous (IV) administration apparatus (1) and more particularly to a mobile intravenous (IV) administration apparatus (1) that can be fasten to a human body. The apparatus (1) is having a holder assembly (2) which pivotedly holding IV drip bag (4) such that the IV drip bag (4) may swing freely and maintain in its upright position regardless of the movement of the patient. The top cover of the holder assembly (2) may be raised or lowered to fit different sizes of IV drip bag (4).

10 Claims, 3 Drawing Sheets

MOBILE INTRAVENOUS ADMINISTRATION APPARATUS

CLAIM OF PRIORITY

This is a national phase application and claims priority to PCT Application No. PCT/MY2010/000290 filed on Nov. 24, 2010 based on Malaysian Patent Application No. PI20094994 filed on Nov. 24, 2009.

FIELD OF TECHNOLOGY

This invention relates to administration of intravenous (IV) fluid into a human body and more particularly to an apparatus which can be fastened to human body and pivotedly holding an IV drip bag such that the IV fluid could be supplied to the human body continuously even when he is in the move.

BACKGROUND

Ambulation for the in-hospital patient is a common occurrence. In fact early ambulation of the post-surgical patient has been shown to decrease respiratory morbidity in the post operative period. However, the patients in most need of early ambulation are usually those who have intravenous (IV) infusions in place. Ambulation for such patients can be difficult since they are usually required to push a wheeled IV pole having a large IV fluid bag attached. The IV pole usually is quite tall in order to establish a sufficient pressure gradient while the patient is in the upright position. Also, the pole must have a wide base to increase its stability.

There are many instances where it is desirable to attach one or more pieces of equipment together to form a movable assembly. For example, hospital patients are generally placed in a wheeled hospital bed so that the patients can be moved from one location to another, such as to and from various hospital wards. These patients often have one or more pieces of medical equipment located near the bed for providing various treatments. One such piece of equipment is an intravenous drip bag mounted on a pole extending from a wheeled base or cart (IV pole). When transporting a patient it is usually preferable to keep the IV pole with the patient so as to maintain the flow of solution from the drip bag to the patient. However, transporting a patient coupled to an IV sometime require additional medical personnel to ensure that the IV pole safely accompanies the patient.

The height of the pole and the breadth of the base can lead to difficult and dangerous ambulation conditions for the patient. Numerous incidents had occurred associating patient and/or visitor injuries resulting from such ambulatory IV poles. Aside from the dangers associated with the use of such IV poles for ambulatory patients, these poles also lack convenience. For example, it is difficult to carry items, such as cafeteria trays, while pushing such an IV pole.

Accordingly, in order to eliminate the need for the additional personnel, there is a need for improved IV delivery systems that are, for example specially adapted for ambulatory patients. Such improved systems would ideally provide added safety and convenience for the patient.

SUMMARY

Accordingly, it is an object of the present invention to provide a mobile intravenous (IV) administration apparatus.

It is another object of the present invention to provide a mobile intravenous (TV) administration apparatus that may be worn by a patient.

It is another object of the present invention to provide a mobile intravenous (IV) administration apparatus that may be worn by a patient capable of accommodating various sizes of IV drip bottle.

These and other objects of the present invention are achieved by,

A mobile intravenous (IV) administration apparatus (1) comprising:

a holder assembly (2); and a body strap (3), characterized in that, said holder assembly (2) is adapted to removably secure an IV drip bottle (4) and said IV drip bottle (4) may swing freely and maintained in its upright position regardless of the movement of a patient when using said mobile intravenous administration apparatus (1).

Preferably, said holder assembly (2) have a pair of support members (5) having serration at both sides.

More preferably, said holder assembly (2) having a pair of sliders (6) with stoppers adapted for engagement with the serrations on said support members (5).

More preferably, said bolder assembly (2) having a timer (9) to set an alarm to warn the patient.

BRIEF DESCRIPTION OF THE DRAWINGS

Other aspect of the present invention and their advantages will be discerned after studying the Detailed Description in conjunction with the accompanying drawings in which.

DETAILED DESCRIPTION

Figure 1:
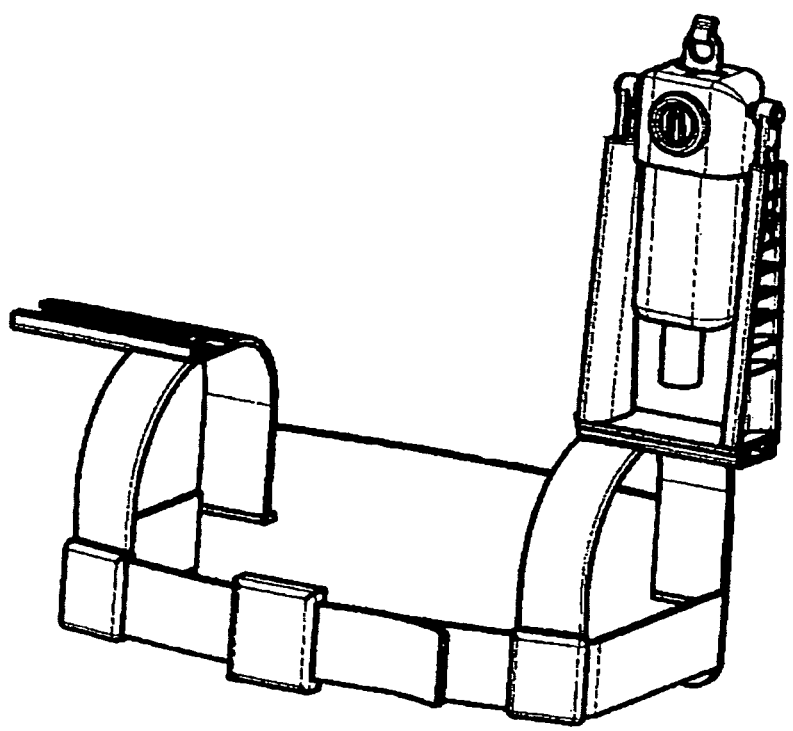
FIG. 1 shows complete assembly of the present invention.
Figure 2:
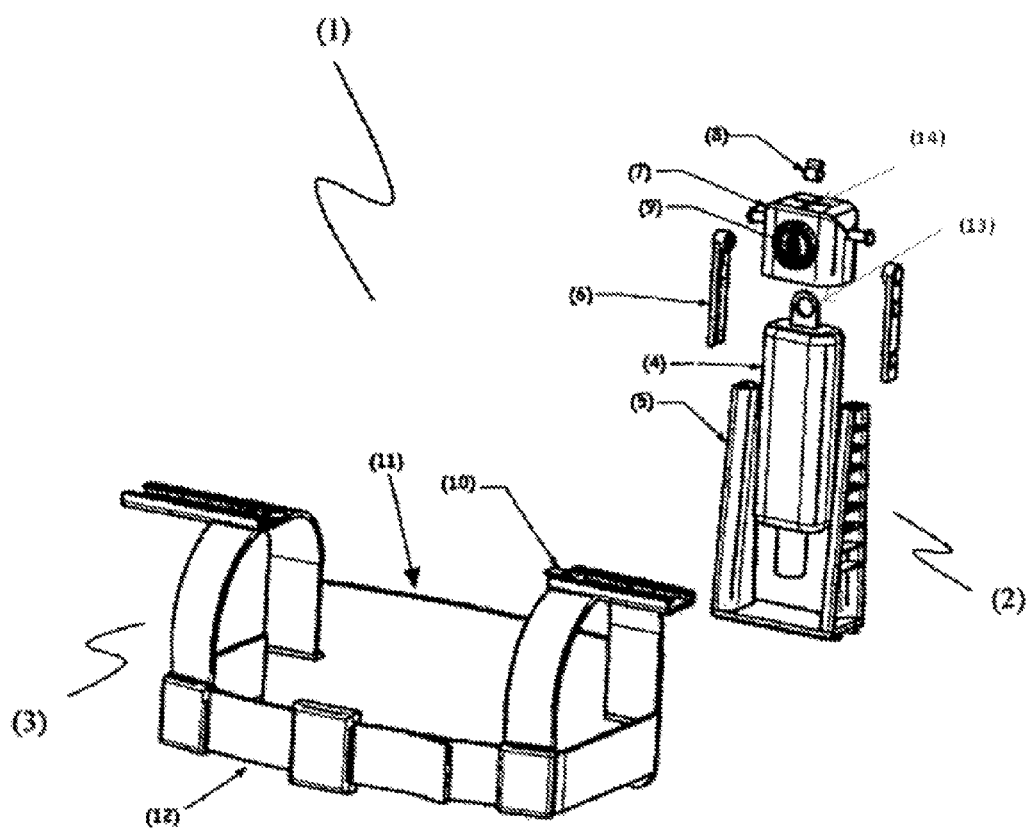
FIG. 2 shows exploded view of the present invention.
Figure 3:
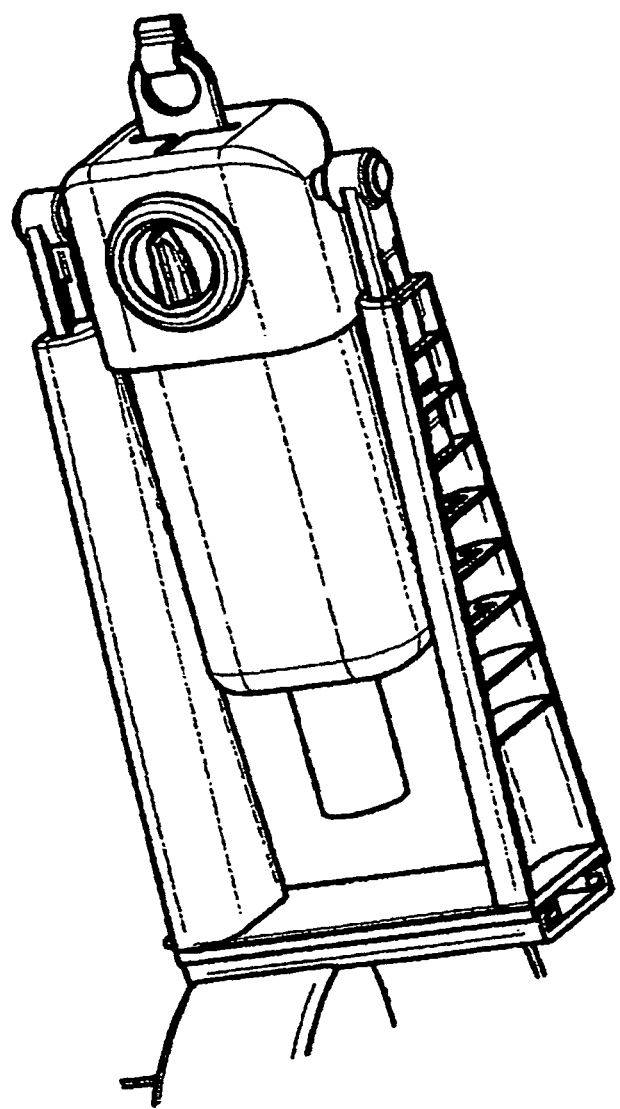
FIG. 3 shows enlarge view of embodiment of the present invention.

The present invention relates to an intravenous (FV) administration apparatus (1) to supply IV fluids consistently into an ambulatory patient where the apparatus (1) can be worn by the patient like a back pack. FIG. 1 shows an assembled apparatus (1) of the present invention with an IV drip bag (4) positioned on the left hand side of the apparatus (1). The exploded view showing individual parts in details is shown in FIG. 2. As shown in both figures, the apparatus (I) comprises of a body strap (3) and a holder assembly (2). The body strap (3) acts as a base for the holder assembly (2) and to be worn by a patient. The holder assembly (2) is to secure the IV drip bag (4). There are two base guides (10) disposed on the body strap (3), one on the right hand side and the other one is on the left hand side and they are for allowing mounting of the holder assembly (2) to the body strap (3). The base of the holder assembly (2) and the base guides (10) are designed in such a way for engagement with each other.

The body strap (3) comprises of a backrest support (11), preferably cushion like, and strap means (12) with buckle as normally found in car seat belt, air plane seat belt or the like. The backrest support (11) is having shoulder rest to support patient's shoulders with the base guides (10) rested on each shoulder. The base guides (10) are made of rigid materials such as metal, hard rubber, hard plastic or the like so as to maintain unbendable when the holder assembly (2) with the IV drip bag (4) are fasten. Preferably the base sliders (10) are provided having locking means so that the holder assembly (2) is firmly stands.

The holder assembly (2) is preferably made of rigid material such as metal, hard rubber, hard plastic or the like and comprises of individual parts and these parts are support member (5), sliders (6), a top cover (7), a locking clip (8) and a timer (9). The support member (5) is having serration on its two arms for engagement with the sliders (6) and the base of the support member (5) is for engagement with the base guides (10) of the body strap (3). The top cover (7) is preferably in cup shape with a slit (14) of "+" shaped at the base. The top cover (7) is having an outwardly protrusions at the sides, where these outward protrusions are for engagement with the apertures of the sliders (6). A conventional IV drip bag has an aperture (13) for hooking onto a pole to keep the IV drip bag hanging. In the present invention, the aperture (13) on the IV drip bag (4) is slide in the "+" shape slit (14) and clamped by the locking clip (8) to hold the IV fluid bag hanging. The timer (9) is disposed on the top cover (7) to operate as an alarm to turn off the apparatus (1) so that the patient is able to control the amount of fluid being injected into the patient's body.

The serration of the support member (5) and the pair of sliders (6) are to accommodate each other to control elevation of the top cover (7) which holds the IV drip bag (4). This to ensure that the assembly (1) is able to accommodate various sizes of IV drip bags (4). The sliders (6) are elevated accordingly depending on the size of the IV drip bag (4). The sliders (6) are squeezable so that they are able to be moved ups and downs during elevation and the stoppers disposed on the sliders (6) are for abutting the serration of the support members (5) to hold the top cover (7) in place.

It may be understood that the IV drip bag (4) is hanging like a pendulum and maintain its upright position regardless of the movement of the patient. The sliders (6) may be elevated accordingly so that the IV drip bag (4) in different sizes may be fitted in the holder assembly (2).

With the mobile intravenous (IV) administration apparatus (1) as proposed by the present invention may be worn by a patient, the patient will have continuous supply of IV fluid even while on the move. Further, the holder assembly (2) pivotedly secured the IV drip bag (4) thus maintaining it in upright position regardless of the movement of the patient. The freely swing feature of the IV drip bag (4) is advantageous as the patient may move freely including bending without the IV drip bag (4) dropped. However, the holder assembly (2) is not limited to single planar swinging movement only. This is depends on the mechanical joint, for example ball bearing and socket which may offer multi planar swinging.

While a particular form of the present invention has been illustrated and described, it will be apparent that many varying embodiments with various modification can be made without departing from the scope of the invention. Therefore, it is understood that the detail herein are to be interpreted as illustrative and not in a limiting sense.

What is claimed is:

1. A mobile intravenous (IV) administration apparatus comprising:
    a holder assembly; and
    a body strap,
    characterized in that, said holder assembly comprises:
        a top cover for holding an IV drip bottle, wherein an aperture on the IV drip bottle is clamped by a locking clip of the top cover to hold the IV drip bottle securely;
        a pair of support members extending from a base and forming a U-shaped holder assembly; and
        a pair of sliders for engaging the pair of support members and the top cover; wherein said top cover is adapted to pivot relative to said support members; and wherein said holder assembly is adapted to removably secure an IV drip bottle such that said IV drip bottle may swing freely about a pivot such that its upright position is maintained regardless of the movement of a patient using said mobile intravenous administration apparatus.

2. A mobile intravenous (IV) administration apparatus as claimed in claim 1, further characterized in that said holder assembly and said body strap are removably secured to each other.

3. A mobile intravenous (IV) administration apparatus as claimed in claim 1, further characterized in that said top cover is held upright on said holder assembly.

4. A mobile intravenous (IV) administration apparatus as claimed in claim 1, further characterized in that said U-shaped holder assembly has serrations formed along its support member and is adapted for engagement with a slider.

5. A mobile intravenous (IV) administration apparatus as claimed in claim 1, further characterized in that said top cover has extended protrusions formed on each side for engagement with apertures on said sliders.

6. A mobile intravenous (IV) administration apparatus as claimed in claim 4, further characterized in that said slider is adapted to slide in and out of said support member of said holder assembly for fitting various sizes of the IV drip bottle.

7. A mobile intravenous (IV) administration apparatus as claimed in claim 2, further characterized in that said body strap has at least one base to couple to the base of said holder assembly.

8. A mobile intravenous (IV) administration apparatus as claimed in claim 2, further characterized in that said body strap has a strap to secure the apparatus onto a human body.

9. A mobile intravenous (IV) administration apparatus as claimed in claim 8, further characterized in that said strap is made of strong fiber or fabric.

10. A mobile intravenous (IV) administration apparatus as claimed in claim 1, further characterized in that said aperture on said IV drip bottle is positioned in a cross-shaped slit of said top cover.

* * * * *